United States Patent
Chen et al.

(10) Patent No.: US 6,756,051 B1
(45) Date of Patent: Jun. 29, 2004

(54) BIOADHESIVE, CLOSED-CELL FOAM FILM, SUSTAINED RELEASE, DELIVERY DEVICES AND METHODS OF MAKING AND USING SAME

(76) Inventors: Li-Lan H. Chen, 3906 Victoria Ct., Edison, NJ (US) 08817; Li Tao, 492 Horizon Dr., Edison, NJ (US) 08817; Alfred Liang, 25 Park Gate Dr., Edison, NJ (US) 08820; Xu Zheng, 5 Koster Blvd. Apt #2B, Edison, NJ (US) 08837

( * ) Notice: Subject to any disclaimer, the term of this patent is extended or adjusted under 35 U.S.C. 154(b) by 0 days.

(21) Appl. No.: 09/713,548

(22) Filed: Nov. 15, 2000

(51) Int. Cl.[7] .......................... A01N 25/34; A61F 13/00; A61F 13/02; A61L 15/16
(52) U.S. Cl. .................. 424/443; 424/422; 424/434; 424/435; 424/448; 424/449; 424/430; 424/447
(58) Field of Search .............................. 424/422, 448, 424/447, 449, 434, 435, 443, 402, 430

(56) References Cited

U.S. PATENT DOCUMENTS

| | | | |
|---|---|---|---|
| 4,517,173 A | * | 5/1985 | Kizawa et al. ................ 424/16 |
| 4,572,832 A | | 2/1986 | Kigasawa et al. |
| 4,629,621 A | | 12/1986 | Snipes |
| 4,713,243 A | | 12/1987 | Schiraldi et al. |
| 4,740,365 A | * | 4/1988 | Yukimatsu et al. ......... 424/435 |
| 4,765,983 A | | 8/1988 | Takayanagi et al. |
| 4,772,470 A | | 9/1988 | Inoue et al. |
| 4,777,046 A | | 10/1988 | Iwakura et al. |
| 4,876,092 A | | 10/1989 | Mizobuchi et al. |
| 4,900,552 A | | 2/1990 | Sanvordeker et al. |
| 5,047,244 A | | 9/1991 | Sanvordeker et al. |
| 5,137,729 A | | 8/1992 | Kuroya et al. |
| 5,456,745 A | | 10/1995 | Roreger et al. |
| 5,458,884 A | | 10/1995 | Britton et al. |
| 5,516,523 A | | 5/1996 | Heiber et al. |
| 5,650,192 A | | 7/1997 | Britton et al. |
| 5,700,478 A | | 12/1997 | Biegajski et al. |
| 5,891,458 A | | 4/1999 | Britton et al. |
| 5,900,247 A | | 5/1999 | Rault et al. |

FOREIGN PATENT DOCUMENTS

EP 0530861 A2 * 4/1987
WO 97/42941 11/1997

* cited by examiner

Primary Examiner—James M. Spear
Assistant Examiner—Sharon Howard
(74) Attorney, Agent, or Firm—Dechert, LLP; John W. Ryan

(57) ABSTRACT

Bioadhesive, closed-cell foam film, sustained release, delivery devices for administering an active agent or combination of active agents to a subject are provided. Methods for making such delivery devices and to methods for using such delivery devices offering the controlled and sustained release of an active agent or combination of active agents to a subject, preferably a near zero-order release, are also provided.

21 Claims, 1 Drawing Sheet

BIOADHESIVE, CLOSED-CELL FOAM FILM, SUSTAINED RELEASE, DELIVERY DEVICES AND METHODS OF MAKING AND USING SAME

The present invention relates to bioadhesive, closed-cell foam film, sustained release, delivery devices for administering an active agent or combination of active agents to a subject. The present invention also relates to methods for making such delivery devices and to methods for using such bioadhesive delivery devices to provide a sustained, controlled release of an active agent or combination of active agents to a subject, preferably a near zero-order release of the active agent or combination of active agents.

Prescription and over-the-counter medications and other pharmaceutical products have traditionally been administered through oral ingestion, nasal sprays, injections and suppositories. For example, many pharmaceutical dosage forms are administrated orally in the form of solid shaped articles such as tablets, pills, caplets and capsules that retain their shape under moderate pressure. Generally these dosage forms are designed to be swallowed whole or chewed to deliver the medication with adequate amounts of liquid. Some patients, particularly pediatric and geriatric patients, have difficulty swallowing or chewing such solid dosage forms. Certain patients such as children or animals often resist taking medications, and may try to hide such dosage forms in order to spit it out later. In addition, many pediatric and geriatric patients are unwilling to take such solid dosage forms because they have difficulty swallowing them even when liquids are consumed therewith. Furthermore, the availability of liquids at the time of administering medications may be limited for certain patients and may be restricted for certain diseases and/or treatments.

Chewable tablets provide some advantages over conventional tablets. Such chewable tablets, however, are not suitable for children wearing braces and the taste of certain active agents may be unpleasant and difficult to mask in a chewable tablet. In addition, the use of chewable tablets may not eliminate the desire or need to administer water or some other liquid therewith.

Furthermore, the standard oral dosage forms, such as tablets, pills, caplets, and capsules, are designed for short residence time in the mouth. Absorption of the active agent from these dosage forms typically occurs in the gastrointestinal (GI) tract, after the active agent has separated from the dosage form and dissolved in the gastric fluids. For some active agents, it is desirable to achieve absorption through a mucosal tissue in order to accelerate onset of the therapeutic effect.

Many active agents are poorly absorbed, even after they are dispersed in the stomach, because of low solubility or slow dissolution rate in the gastric fluids. Tablets may be formulated so as to be quick dissolving. These tablets are commonly placed on the tongue and disintegrate rapidly in the oral cavity. These dosage forms, however, are not fixed to a mucosal tissue and may move around in the mouth. Consequently, these dosage forms do not overcome the risk associated with choking or gagging that occurs with subjects having limited control of their swallowing reflexes.

Accordingly, what is needed are bioadhesive delivery devices which provide for the sustained, controlled release of an active agent or combination of active agents to a subject, which delivery devices are easy to use and are comfortable while in place in a subject.

Glossary

The following definitions are provided to facilitate an understanding of certain terms used frequently herein.

The term "bioadhesive delivery device" as used herein and in the appended claims means any solid substance, of any shape, which is intended to be adhered to a mucosal tissue of a subject. The term "buccal device" or "buccal delivery device" means a bioadhesive device which is intended to be inserted into the buccal cavity. The term "vaginal device" or "vaginal delivery device" means a bioadhesive device which is intended to be inserted into the vagina.

The term "bioadhesive, closed-cell foam film, sustained release, delivery device" as used herein and in the appended claims means a bioadhesive delivery device comprising a closed-cell foam film substance designed to provide a sustained, controlled release an active agent or combination of active agents to a subject. These bioadhesive delivery devices preferably include buccal delivery devices and vaginal delivery devices.

The term "controlled release" as used herein and in the appended claims means that a predetermined dosage of an active agent or combination of active agents is administered to a subject over a period of time.

The term "bioadhesive force" as used herein and in the appended claims is a quantitative value for tackiness (grams) which simulates the adhesion of the bioadhesive, closed-cell foam film, sustained release, delivery devices of the present invention upon contact with a moist mucosal tissue. The bioadhesive force preferably should be at least 10 grams, more preferably at least 15 grams, most preferably at least 20 grams.

The term "% elongation" as used herein and in the appended claims is measured when a bioadhesive, closed-cell foam film, sustained release, delivery device of the present invention snaps as sufficient force is applied to exceed the elastic limit thereof.

The term "modulus" as used herein and in the appended claims is a measurement of the stiffness of a bioadhesive, closed-cell foam film, sustained release, delivery device of the present invention.

The term "mucosal tissue" as used herein and in the appended claims means any moist mucosal surface of the subjects body as deemed appropriate for the systemic or local delivery of an active agent or combination of active agents including oral, nasal, vaginal, rectal and ocular tissues. The term "oral tissue(s)" as used herein and in the appended claims includes lingual, sub-lingual, buccal, gingival and palatal surfaces; most preferably lingual, sub-lingual and buccal surfaces.

The term "permeation enhancer" as used herein and in the appended claims means a natural or synthetic molecule which facilitates the absorption of a given active agent or combination of active agents through a mucosal tissue.

The term "release period" as used herein and in the appended claims means the period of time subsequent to administration of a bioadhesive, closed-cell foam film, sustained release, delivery devices of the present invention during which the delivery device releases an active agent or combination of active agents to a subject.

The term "subject" as used herein and in the appended claims means an animal, preferably a mammal, most preferably a human.

The term "sustained release" as used herein and in the appended claims means the continual release of an active agent or combination of active agents over a period of time.

The term "tensile strength" as used herein and in the appended claims is expressed in pounds per square inch (psi) and is the property of a bioadhesive, closed-cell foam film, sustained release, delivery device of the present invention that requires a load to cause load deformation failure of said film.

The term "thickness" as used herein and in the appended claims by measurements in mil (a mil=one thousandth of an inch) is determined when a bioadhesive, closed-cell foam film, sustained release, delivery device of the present invention is placed between two microscopic slides.

The term "water content" as used herein and in the appended claims is the % residual water content per unit dose as measured to the Karl Fisher method and expressed as percent of the dry weight of a bioadhesive, closed-cell foam film, sustained release, delivery device of the present invention.

The term "zero order release" in relation to release kinetics as used herein and in the appended claims means that the rate of release of the active agent or active agents from a delivery device is a linear function with time.

SUMMARY OF THE INVENTION

In a preferred embodiment of the present invention, bioadhesive, closed-cell foam film, sustained release, delivery devices are provided which contain: (a) an active agent or combination of active agents, (b) a nonionic polymer or combination of nonionic polymers, (c) an anionic polymer or combination of anionic polymers, (d) a softening agent or combination of softening agents, (e) a swelling modifier or combination of swelling modifiers, (f) a chelating agent or combination of chelating agents, (g) a buffering agent or combination of buffering agents and (h) a foaming agent or combination of foaming agents. In a preferred aspect of this embodiment, the mass ratio of (i) the nonionic polymer or combination of nonionic polymers to (ii) the an anionic polymer or combination of anionic polymers in the delivery devices of the present invention preferably should be in the range of 1:6 to 6:1. In another preferred aspect of this embodiment, the mass ratio of (i) the swelling modifier or combination of swelling modifiers to (ii) the combination of the nonionic polymer or combination of nonionic polymers and the anionic polymer or combination of anionic polymers in the delivery devices of the present invention preferably should be in the range of 1:100 to 1:10. In yet another preferred aspect of this embodiment, the delivery devices of the present invention comprise multiple layers; most preferably, the delivery devices of the present invention preferably comprise a single layer. In still another preferred aspect of this embodiment, the delivery devices of the present invention preferably have a density of at least 0.2 grams/cm$^3$; most preferably, the delivery devices of the present invention have a density in the range of 10 to 90% of the density of an identical non-foamed composition.

The bioadhesive, closed-cell foam film, sustained release, delivery devices of the present invention preferably contain 0.01 to 50 wt % of an active agent or combination of active agents.

The bioadhesive, closed-cell foam film, sustained release, delivery devices of the present invention preferably contain 10 to 60 wt % of a nonionic polymer or combination of nonionic polymers.

The bioadhesive, closed-cell foam film, sustained release, delivery devices of the present invention preferably contain 10 to 60 wt % of an anionic polymer or combination of anionic polymers.

The bioadhesive, closed-cell foam film, sustained release, delivery devices of the present invention preferably contain 5 to 40 wt % of a softening agent or combination of softening agents.

The bioadhesive, closed-cell foam film, sustained release, delivery devices of the present invention preferably contain 0.1 to 10 wt % of a swelling modifier or combination of swelling modifiers.

The bioadhesive, closed-cell foam film, sustained release, delivery devices of the present invention preferably contain 0.01 to 5 wt % of a chelating agent or combination of chelating agents.

The bioadhesive, closed-cell foam film, sustained release, delivery devices of the present invention preferably contain 0.1 to 10 wt % of a buffering agent or combination of buffering agents.

The bioadhesive, closed-cell foam film, sustained release, delivery devices of the present invention preferably contain 0.1 to 5 wt % of a foaming agent or combination of foaming agents.

The bioadhesive, closed-cell foam film, sustained release, delivery devices of the present invention may optionally contain additional ingredients, including: taste modifying agents, coloring agents, preservatives and permeation enhancers.

In another preferred embodiment of the present invention, bioadhesive, closed-cell foam film, sustained release, delivery devices are provided which contain: (a) 0.01 to 50 wt % of an active agent or combination of active agents, (b) 10 to 60 wt % of a nonionic polymer or combination of nonionic polymers, (c) 10 to 60 wt % of an anionic polymer or combination of anionic polymers, (d) 5 to 40 wt % of a softening agent or combination of softening agents, (e) 0.1 to 10 wt % of a swelling modifier or combination of swelling modifiers, (f) 0.01 to 5 wt % of a chelating agent or combination of chelating agents, (g) 0.1 to 10 wt % of a buffering agent or combination of buffering agents and (h) 0.1 to 5 wt % of a foaming agent or combination of foaming agents. In a preferred aspect of this embodiment, the mass ratio of (i) the nonionic polymer or combination of nonionic polymers to (ii) the anionic polymer or combination of anionic polymers in the delivery devices of the present invention preferably should be in the range of 1:6 to 6:1. In another preferred aspect of this embodiment, the mass ratio of (i) the swelling modifier or combination of swelling modifiers to (ii) the combination of the nonionic polymer or combination of nonionic polymers and the anionic polymer or combination of anionic polymers in the delivery devices of the present invention preferably should be in the range of 1:100 to 1:10. In yet another preferred aspect of this embodiment, the delivery devices of the present invention may comprise multiple layers. Most preferably, the delivery devices of the present invention comprise a single layer. In still yet another preferred aspect of this embodiment, the delivery devices of the present invention preferably have a density of at least 0.2 grams/cm$^3$. Most preferably, the delivery devices of the present invention preferably have a density in the range of 10 to 90% of the density of an identical non-foamed composition.

In another embodiment of the present invention, a method for delivering an active agent or combination of active agents to a subject is provided, wherein a bioadhesive, closed cell foam film, sustained release, delivery device is administered to a mucosal tissue of the subject; wherein the delivery device contains: (a) 0.01 to 50 wt % of an active agent or combination of active agents, (b) 10 to 60 wt % of a nonionic polymer or combination of nonionic polymers, (c) 10 to 60 wt % of an anionic polymer or combination of anionic polymers, (d) 5 to 40 wt % of a softening agent or combination of softening agents, (e) 0.1 to 10 wt % of a swelling modifier or combination of swelling modifiers, (f) 0.01 to 5 wt % of a chelating agent or combination of chelating agents, (g) 0.1 to 10 wt % of a buffering agent or combination of buffering agents and (h) 0.1 to 5 wt % of a foaming agent or combination of foaming agents; and wherein the delivery device adheres to the mucosal tissue. In a preferred aspect of this embodiment, the mucosal tissue to which the delivery device is adhered is selected from the group including: oral, nasal, vaginal, rectal and ocular tissues; most preferably oral or vaginal tissues. In another preferred aspect of this embodiment, the delivery device provides a sustained, controlled release of an active agent or combination of active agents to the subject for a release period of at least 10 minutes, more preferably for a release period of 10 minutes to 168 hours, most preferably for a release period of at least 3 hours to a few days depending on the site of application. In another preferred aspect of this embodiment, the release kinetics of the active agent or combination of active agents from the delivery device should be near zero-order. In yet another preferred aspect of this embodiment, the delivery device completely dissolves or erodes from the mucosal tissue to which it is administered without leaving a residue. In still another preferred aspect of this embodiment, the delivery device releases the active agent or combination of active agents from all external surfaces of the delivery device.

BRIEF DESCRIPTION OF THE DRAWING

There are shown in the drawings certain exemplary embodiments of the present invention as presently preferred. It should be understood that the present invention is not limited to the embodiments disclosed as examples, and is capable of variation within the spirit and scope of the appended claims.

In the drawings.

DETAILED DESCRIPTION

Figure 1:
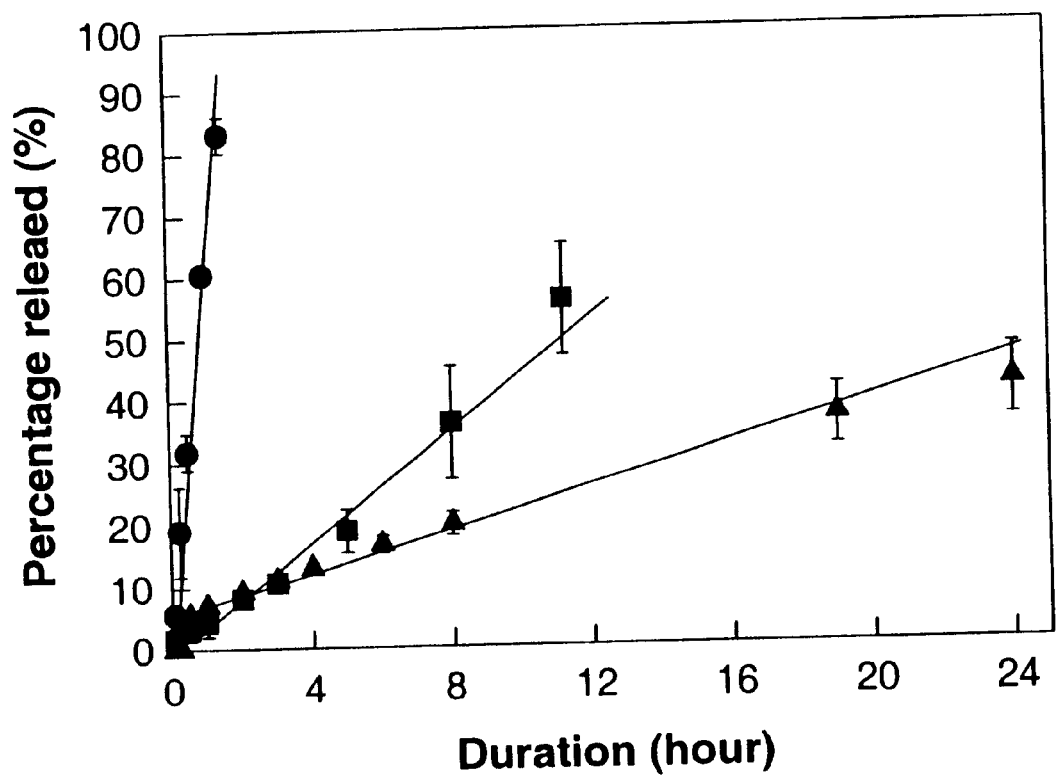
FIG. 1 is a graphical depiction of the release profiles for estradiol from three different bioadhesive, closed-cell foam film, sustained release, delivery devices of the present invention.

The bioadhesive, closed-cell foam film, sustained release, delivery devices of the present invention may release an active agent or combination of active agents over a release period which is determined by a number of different factors. These factors include the dimensions of the film, the concentration of the active agent or combination of active agents, the solubility of the active agent or combination of active agents at the mucosal tissue to which the delivery device is adhered, how the active agent or combination of active agents is dispersed within the delivery device and the density of the delivery device.

The thickness of the delivery device is a factor in determining the rate of dissolution. A thick delivery device will dissolve more slowly than an otherwise similar thin delivery device. A thick delivery device may be desirable over a similar thin delivery device for larger dosages of active agent based on the relative holding capacity of such devices.

The extent of the uptake of the active agent or combination of active agents from the delivery device at the site of application can be controlled by the dissolution rate of the delivery device. The delivery device of the present invention release the active agent or combination of active agents contained therein as the delivery device dissolves or erodes. Once released from the delivery device, the active agent or active agents may be absorbed by the mucosal tissue at or in proximity to the site of application or may be carried away to another location in the subject where it can be absorbed. For example, the active agent or active agents may be rapidly released by the delivery device into the mouth of a subject after which much of the active agent or active agents is/are subsequently swallowed and taken up in the gastrointestinal tract. In contrast, the active agent or active agents may be slowly released by the delivery device into the mouth of a subject in proximity to mucosal tissue giving rise to an increased uptake of the active agent or active agents through the mucosal tissue.

A further parameter affecting the release of an active agent or combination of active agents from the bioadhesive, closed-cell foam, sustained release, delivery devices of the present invention is the manner in which the active agent or combination of active agents is dispersed in the delivery device. For example, the active agent or combination of active agents may be dispersed as colloidal particles or be microencapsulated within the delivery device or alternatively may be mixed throughout the delivery device as a reagent during casting.

Yet another parameter affecting the release of an active agent or combination of active agents from the bioadhesive, closed-cell foam, sustained release, delivery devices of the present invention is the volume of entrapped gas bubbles in the delivery device. The entrapment of gas bubbles within the delivery devices of the present invention increases the fragility of those devices upon swelling when placed in contact with a mucosal tissue. This fragility of the delivery devices affects the rate at which they dissolve and/or erode when administered to a subject. That is, the extent to which a delivery device is foamed, i.e. the volume of gas entrapped within the delivery device, is a design feature which can be used to modify the release kinetics of the active agent or combination of active agents released from the delivery device upon administration to a mucosal tissue of a subject. Specifically, the greater the reduction in the density of the delivery device (i.e., the larger the volume of gas incorporated therein) the more rapidly the delivery device with dissolve/erode when administered to a subject.

The bioadhesive, closed-cell foam film, sustained release, delivery devices of the present invention are formulated and designed to adhere to various tissue surfaces, preferably mucosal epithelia. Depending on the design and purpose of a given delivery device, the site of adhesion may also be the site of administration for the active agent or combination of active agents incorporated into the delivery device. To provide stable bioadhesiveness over a broad range of both acidic and basic pH, nonionic water soluble polymers having hydroxyl functional groups are combined with anionic polymers to reduce the pH effect on the hydration, swelling and bioadhesion of the resulting polymer mix. The mixture of anionic and nonionic polymers is believed to result in hydrogen bonding which leads to a strong cross-linking force between the polymers. The ratio of anionic and nonionic polymers is a design feature which can be used to alter the release characteristics of the active agent or combination of active agents from the delivery devices of the present invention. It is also believed that the combination of non-ionic polymers and anionic polymers can be selected such that the resulting polymeric matrix exhibits hydration, swelling, drug release and bioadhesion characteristics which are insensitive to the anticipated pH ranges to which the delivery devices will be exposed upon administration to the subject.

A swelling modifier or combination of swelling modifiers, which may include retarders and promoters, are preferably used in the delivery devices of the present invention to further control the hydration rate, the degree of swelling and the release kinetics those delivery devices. The anionic polymer(s), nonionic polymer(s) and swelling modifier(s) used in the delivery devices of the present invention preferably should be homogeneously mixed at the molecular level through the aid of a suitable solvent.

A chelating agent or combination of chelating agents are preferably used in the delivery devices of the present invention to serve as a stabilizer, enzymatic inhibitor and absorption enhancer in those delivery devices.

A buffering agent or combination of buffering agents are preferably incorporated into the bioadhesive, closed-cell foam film, sustained release, delivery devices of the present invention to modulate the pH at the site of application and to reduce the incidence of mucosal irritation which might otherwise result from the acidity of the anionic polymers included in the delivery devices. The use of buffering agents in the delivery devices of the present invention may also help facilitate a near zero-order release of the active agent or combination of active agents from the delivery device by modulating the pH at the site of application.

A softening agent or combination of softening agents are preferably incorporated into the bioadhesive, closed-cell foam film, sustained release, delivery devices of the present invention. The incorporation of softening agents into the delivery devices helps to soften the delivery device, thereby reducing the contact angle between the delivery device and the mucosal tissue to which it is to be adhered. That is, the softening agent helps to insure that the delivery device will be sufficiently soft and pliable to enable the delivery device to conform to the surface contours of the mucosal tissue to which it is to be adhered.

A foaming agent or combination of foaming agents are preferably incorporated into the bioadhesive, closed-cell foam film, sustained release, delivery devices of the present invention. The foaming agents operate to stabilize the air bubbles introduced into the delivery device during manufacture.

Preferred bioadhesive, closed-cell foam film, sustained release, delivery devices of the present invention exhibit the following characteristics, namely (a) they should be sufficiently flexible to adapt to the opening exposing, and the surface of, the mucosal tissue to which they are adapted to be administered, (b) they should be comfortable and unobstructive during use, (c) they should be easy to administer to the site of application, (d) they should remain in place on the mucosal tissue without moving once administered thereto, (e) they should be capable of providing a sustained, controlled release of an active agent or combination of active agents, preferably, a zero-order release; (f) they should not cause irritation and (g) they should be completely dissolved and/or eroded at the end of the release period without the need for the physical removal of a residue.

The bioadhesive, closed-cell foam film, sustained release, delivery devices of the present invention are intended to be inserted by the subject to be treated and do not require fitting by a physician. They can be easily inserted digitally or with an applicator.

In use, the bioadhesive, closed-cell foam film, sustained release, delivery devices of the present invention are administered to a mucosal tissue of a subject and are maintained in intimate contact with the mucosal tissue for a release period of at least 10 minutes, preferably for a release period of 10 minutes to 168 hours, most preferably for a release period of at least 3 hours to a few days, depending on the site of application, following in vivo placement of the delivery device. Upon contact with the moist mucous tissue of the subject, the delivery device naturally and slowly begins to dissolve and/or erode. As the delivery device dissolves and/or erodes, it continually releases an active agent or combination of active agents at a rate which is sufficient to maintain a therapeutic effect.

The active agent or combination of active agents included in the bioadhesive, closed-cell foam film, sustained release, delivery devices of the present invention may be absorbed through the mucosal tissue at and in proximity to the site of administration of the delivery device, thereby avoiding any undesirable hepatic first-pass metabolism and gastrointestinal incompatibility associated with the active agent or combination of active agents. It will be recognized, however, that the active agent or combination of active agents can also be absorbed locally in the body cavity. For example, one skilled in the art will recognize that a vaginal delivery device can be used, for example, to administer an antifungal or other active agent for local treatment of, for example, vaginal infections such as yeast and bacterial infections.

The bioadhesive, closed-cell foam film, sustained release, delivery devices of the present invention preferably exhibit good adhesion to the mucosal tissue of the subject to which they are intended to be administered. Upon contact with the mucus which is excreted by the mucosal tissue, the delivery device preferably hydrates and adheres to the mucosal tissue. This feature permits the delivery devices of the present invention to be worn comfortably by the subject and to maintain the delivery device in a proper position to facilitate the sustained, controlled delivery of an active agent or combination of active agents to the subject.

The bioadhesive, closed-cell foam film, sustained release, delivery devices of the present invention contain: (a) an active agent or combination of active agents, (b) a nonionic polymer or combination of nonionic polymers, (c) an anionic polymer or combination of anionic polymers, (d) a softening agent or combination of softening agents, (e) a swelling modifier or combination of swelling modifiers, (f) a chelating agent or combination of chelating agents, (g) a buffering agent or combination of buffering agents and (h) a foaming agent or combination of foaming agents. The mass ratio of (i) nonionic polymer or combination of nonionic polymers to (ii) anionic polymer or combination of anionic polymers contained in the delivery device preferably should be in the range of 1:6 to 6:1. The mass ratio of (i) the swelling modifier or combination of swelling modifiers to (ii) the combination of the nonionic polymer or combination of nonionic polymers and anionic polymer or combination of polymers preferably should be in the range of 1:100 to 1:10. The delivery devices of the present invention may be multilayer devices. Preferably, the deliver devices of the present invention are single layer devices.

The bioadhesive, closed-cell foam film, sustained release, delivery devices of the present invention preferably exhibit a density of at least 0.2 grams/cm$^3$. Most preferably, the bioadhesive, closed-cell foam film, sustained release, delivery devices of the present invention have a density in the range of 10 to 90% of the density of an identical non-foamed composition.

The bioadhesive, closed-cell foam film, sustained release, delivery devices of the present invention may be used as a vehicle for delivering a wide range of active agents to a subject. For example, the active agent may include small molecules (i.e., less than 500 daltons), proteins, nucleic acids including antisense molecules or other biological or synthetic molecules. Active agents suitable for use with the present invention include, but are by no means limited to, therapeutic agents, nutritional supplements and hygiene aids.

Therapeutic agents suitable for use with the present invention include, but are not limited to, local and systemic agents such as analgesics, $\alpha$-adrenergic receptor blockers, anti-Alzheimer's disease medications, antianginal, antianxiety, antiarrythmics, antiarthritics, antibiotics, anticoagulants/thrombolytics, anticonvulsants/anti-Parkinson medications, anti-depressants, anti-diabetics, anti-diarrheal, anti-epileptics, anti-fungal, anti-gout, anti-heartworm medications for dogs, anti-histamines, anti-hypertensives, anti-inflammatories, anti-infectives, antimigraines, anti-nausants/anti-emetics, anti-neoplastics/anti-tumor drugs, anti-pruitics, anti-psychotics, anti-pyretics, anti-spasmodics, anti-virals, bronchial dilators/anti-asthmatics, calcium antagonists, cardiac agents, cardiotonics, central nervous system actives, contraceptives, coronary vasodilators, cough/cold remedies, dietary supplements, including vitamins and minerals, diuretics, fertility drugs, flea control agents for animals (Ivermectic), $H_2$ receptor antagonists, herbal actives, hormones, hypoglycemics, hypolipidemics, muscle relaxants, ovulation stimulators, peptide drugs, polypeptide drugs, proteins such as insulin, calcitonin, Luteinizing Hormone Release Hormone ("LHRH") and the like, sedatives and hypnotics, sexual dysfunction drugs, sleep aids, smoking cessation aids, steroids and steroidals, tranquilizers, laxatives, ophthalmic preparations, breath fresheners, breath deodorants, saliva substitutes, antigingivitis agents, anti-cavity agents, anti-plaque agents, diagnostic indicators, and local anesthetics. Also included are drugs for the treatment of osteoporosis, hormone replacement, treatment of periodontal disease, antiseptics, corticosteroids, non steroidal anti-inflammatory agents, antiviral agents and vaccines. Preferably, the bioadhesive, closed-cell foam film, sustained release, delivery devices of the present invention contain 0.01 to 50 wt % of an active agent or combination of active agents.

Nonionic polymers suitable for use with the present invention include, but are by no means limited to, cellulose derivatives such as carboxymethylcellulose, hydroxyethyl cellulose, methylcellulose, hydroxypropyl cellulose and hydroxypropyl methylcellulose; polyvinylpyrrolidone; polyvinyl alcohol; polyethylene oxide; modified starch; gelatin; agar; guar gum; locust bean gum; bentonite and scheroglucan; preferably polyvinylpyrrolidone, hydroxypropyl methylcellulose, hydroxypropyl cellulose, polyvinyl alcohol, gelatin, polyethylene oxide; most preferably, polyvinyl alcohol, gelatin and hydroxypropyl methylcellulose. The nonionic polymer or combination of nonionic polymers included in the bioadhesive, closed-cell foam film, sustained release, delivery devices of the present invention preferably exhibit an equilibrium moisture content of 10 to 20 wt % measured at 20° C. and 75% relative humidity. Preferably, the bioadhesive, closed-cell foam film, sustained release, delivery devices of the present invention contain 10 to 60 wt % of a nonionic polymer or combination of nonionic polymers.

Anionic polymers suitable for use with the present invention include, but are by no means limited to, polyacrylic acid such as carbopol, polycarbophil, poly(methyl vinyl ether-co-methacrylic acid), poly(2-hydroxyethyl methacrylate), poly(methylmethacrylate), poly(isobutylcyanoacrylate), poly(isohexycyanoacrylate) and polydimethylaminoethyl methacrylate; acacia; alginate; carrageenan; guar gum derivative; karaya gum; pectin; tragacanth gum; xanthan gum; dextran; sodium carboxymethylcellulose ("sodium CMC") and hyaluronic acid; preferably carbopol, polycarbophil, alginate, carrageenan, pectin and sodium CMC; most preferably carbopol, polycarbophil, alginate, carrageenan and sodium CMC. The anionic polymer or combination of anionic polymers included in the bioadhesive, closed-cell foam film, sustained release, delivery devices of the present invention preferably exhibit a viscosity of at least 1,000 mPa*s measured at 20° C. for a 1% w/v aqueous solution. Preferably, the bioadhesive, closed-cell foam film, sustained release, delivery devices of the present invention preferably contain 10 to 60 wt % of an anionic polymer or combination of nonionic polymers.

Softening agents suitable for use with the present invention include, but are by no means limited to, propylene glycol, water, polyethylene glycol, glycerin, triacetin, diacetylated monoglyerides, diethyl phthalate and triethyl citrate; preferably propylene glycol, water, glycerin and polyethylene glycol; most preferably water, propylene glycol and glycerin. Preferably, the bioadhesive, closed-cell foam film, sustained release, delivery devices of the present invention contain 5 to 40 wt % of a softening agent or combination of softening agents.

Swelling modifiers suitable for use with the present invention may include either, or both, retarders and promoters. The bioadhesive, closed-cell foam film, sustained release, delivery devices of the present invention preferably contain 0.1 to 10 wt % of a swelling modifier or combination of swelling modifiers.

Retarders suitable for use with the present invention include, but are by no means limited to, wax such as beeswax, carnauba wax, paraffin wax, castorwax, spermaceti, petrolite and microcrystalline wax; polyoxyethylene glyceride fatty acid derivatives; hydrogenated oils and fats such as castor oil, theobroma oil, partially hydrogenated soybean oil, glyceryl laurates, glyceryl myristates, glyceryl palmitates and glyceryl stearates; long chain fatty acids and alcohols such as lauric acid/alcohol, myristic acid/alcohol, palmitic acid/alcohol, stearic acid/alcohol and oleic acid; ethylene glycol distearate; polyoxyethylene sorbitol beeswax derivative; sorbitan esters such as sorbitan tristearate, sorbitan sesquioleate and sorbitan monooleate; propylene glycol monostearate; lecithin and poloxamers; preferably polyoxyethylene glyceride fatty acid derivatives, sorbitan esters, lecithin, poloxamers, wax, hydrogenated vegetable oils; most preferably polyoxyethylene glyceride fatty acid derivatives, sorbitan esters and poloxamers. Preferably the retarder or combination of retarders included in the bioadhesive, closed-cell foam film, sustained release, delivery devices of the present invention are lipophilic. Most preferably, the retarder or combination of retarders exhibit a hydrophilicity lipophilicity balance ("HLB") of 5 or less.

Promoters suitable for use with the present invention include, but are by no means limited to, inorganic electrolytes such as sodium carbonate, sodium bicarbonate, potassium carbonate, potassium bicarbonate, sodium phosphate, potassium phosphate, triethanolamine, aminomethyl propanol, tromethamine, tetrahydroxypropyl ethylenediamine, sodium chloride, magnesium chloride, ferric chloride and aluminum sulfate; preferably sodium bicarbonate, potassium bicarbonate, sodium phosphate, potassium phosphate, triethanolamine, sodium chloride; most preferably sodium bicarbonate, potassium bicarbonate and triethanolamine.

Chelating agents suitable for use with the present invention include, but are by no means limited to, ethylenediaminetetraacetic acid ("EDTA") and salts thereof such as disodium EDTA, tetrasodium EDTA and calsium disodium EDTA; diethylenetriaminepentaacetic acid ("DTPA") and salts thereof; hydroxyethlethylenediaminetriacetic acid ("HEDTA") and salts thereof and nitrilotriacetic acid ("NTA"); preferably EDTA, HEDTA and their salts; most preferably EDTA and its salts. Preferably, the bioadhesive, closed-cell foam film, sustained release, delivery devices of the present invention contain 0.01 to 5 wt % of a chelating agent or combination of chelating agents.

Buffering agents suitable for use with the present invention include, but are by no means limited to, sodium carbonate, sodium bicarbonate, potassium carbonate, potassium bicarbonate, sodium phosphates, potassium phosphates, sodium biphthalate, potassium biphthalate, sodium borate, glycine, tris, triethanolamine, piperazine, acetic acid, citric acid, tartaric acid and phosphoric acid; preferably sodium carbonate, potassium phosphate, citric acid and tartaric acid; most preferably sodium carbonate and citric acid. Preferably, the bioadhesive, closed-cell foam film, sustained release, delivery devices of the present invention contain 0.1 to 10 wt % of a buffering agent or combination of buffering agents.

Foaming agents suitable for use with the present invention include, but are by no means limited to, polyoxyethylene sorbitan esters ("Tweens"), polyoxyethylene alkyl ether ("Brij") and triethanolamine oleate; preferably Tweens and Brij; most preferably Tweens. The foaming agent included in the bioadhesive, closed-cell foam film, sustained release, delivery devices of the present invention preferably exhibit an HLB in excess of 12. Preferably, the bioadhesive, closed-cell foam film, sustained release, delivery devices of the present invention contain 0.1 to 5 wt % of foaming agent or combination of foaming agents.

The bioadhesive, closed-cell foam film, sustained release, delivery devices of the present invention also optionally include taste modifiers, coloring agents, preservatives and permeation enhancers.

Taste modifiers suitable for use with the present invention include flavoring agents, sweetening agents and taste masking agents. Preferred taste modifying agents include the essential oils or water soluble extracts of menthol, wintergreen, peppermint, sweet mint, spearmint, vanillin, cherry, chocolate, cinnamon, clove, lemon, orange, raspberry, rose, spice, violet, herbal, fruit, strawberry, grape, pineapple, peach, kiwi, papaya, mango, coconut, apple, coffee, plum, watermelon, nuts, durean, green tea, grapefruit, banana, butter, chamomile, sugar, dextrose, lactose, mannitol, sucrose, xylitol, malitol, acesulfame potassium, talin, glycyrrhizin, sucralose, aspartame, saccharin, sodium saccharin, sodium cyclamate and honey. Preferably, the bioadhesive, closed-cell foam film, sustained release, delivery devices of the present invention optionally contain 0.01 to 5 wt % of a taste modifier or combination of taste modifiers.

Coloring agents suitable for use with the present invention include, but are by no means limited to, FD & C coloring agents, natural coloring agents, natural juice concentrates and pigments. Preferred pigments include titanium oxide, silicon dioxide and zinc oxide. Preferably, the bioadhesive, closed-cell foam film, sustained release, delivery devices of the present invention optionally contain 0.01 to 5 wt % of a coloring agent or combination of coloring agents.

Preservatives suitable for use with the present invention include, but are by no means limited to, anti-microbial agents and non-organic compounds. Preferred preservatives include sodium benzoate, parabens and derivatives, sorbic acid and salts thereof, propionic acids and salts thereof, sulfur dioxide and sulfites, acetic acid and acetates, nitrites and nitrates. Preferably, the bioadhesive, closed-cell foam film, sustained release, delivery devices of the present invention optionally contain 0.01 to 5 wt % of a preservative or combination of preservatives.

Permeation enhancers suitable for use with the present invention include, but are by no means limited to, a natural or synthetic molecules which facilitate the absorption of an active agent through a mucosal tissue. Preferably, the bioadhesive, closed-cell foam film, sustained release, delivery devices of the present invention optionally contain 0.01 to 5 wt % of a permeation enhancer or combination of permeation enhancers.

In a preferred embodiment of the present invention bioadhesive, closed-cell foam film, sustained release, delivery devices are provided which contain: (a) 0.01 to 50 wt % of an active agent or combination of active agents, (b) 10 to 60 wt % of a nonionic polymer or combination of nonionic polymers, (c) 10 to 60 wt % of an anionic polymer or combination of anionic polymers, (d) 5 to 40 wt % of a softening agent or combination of softening agents, (e) 0.1 to 10 wt % of a swelling agent or combination of swelling agents, (f) 0.01 to 5 wt % of a chelating agent or combination of swelling agents, (g) 0.1 to 10 wt % of a buffering agent or combination of buffering agents and (h) 0.1 to 5 wt % of a foaming agent or combination of foaming agents.

One skilled in the art given the above description of the bioadhesive, closed-cell foam film, sustained release, delivery devices of the present invention will be able to produce those devices using a variety of known processing methods. Preferably, the delivery devices of the present invention are produced using the following described process.

A preferred method for preparing the bioadhesive, closed-cell foam film, sustained release, delivery devices of the present invention involves:

A. Blending or dissolving (i) a nonionic polymer or combination of nonionic polymers and (ii) an anionic polymer or combination of anionic polymers into a suitable solvent to facilitate the formation of hydrogen bonds between the polymers, optionally, applying heat to facilitate the blending/dissolving;

B. Dissolving a swelling modifier or combination of swelling modifiers into a suitable solvent;

C. Dispersing the B into A;

D. Recovering uniform bioadhesive microparticles from C;

E. Blending (i) an active agent or combination of active agents, (ii) a chelating agent or combination of chelating agents, (iii) a buffering agent or combination of buffering agents and (iv) any other optional dry excipients with the recovered microparticles of D to form a powder blend;

F. Wetting the powder blend with a mixture of (i) a foaming agent or combination of foaming agents, (ii) a softening agent or combination of softening agents and (iii) a suitable solvent;

G. Feeding the wetted powder blend to an extruder;

H. Discharging a suitable high pressure gas into the wetted material in the extruder to form a foam;

I. Extruding the foam into a foam film; and,

J. Drying the foam film and cutting it into suitable unit doses.

Preferably, the optional application of heat should not result in the temperature of the blended/dissolved material in A exceeding 50° C.

Preferably, the amount of swelling modifier or combination of swelling modifiers added in B is dictated by the viscosity of the combined solution.

The uniform bioadhesive microparticles of D are preferably obtained by subjecting the product of C to spray drying.

The discharging of high pressure gas into the wetted material in H causes gas bubbles to form within the wetted material resulting in the formation of a closed-cell foam. These gas bubbles remain physically trapped within the final product delivery devices of the present invention. These gas bubbles are in closed-cell form. The density of the delivery devices preferably exceeds 0.2 gram/ml. Most preferably, the delivery devices of the present invention will exhibit a density which is 10 to 90% of the density of an identical non-foamed composition.

Preferred gases suitable for use with the present invention include oxygen and air, most preferably air.

The foamed material in I is preferably extruded into a foamed film which is preferably cast onto a liner and dried. The wet film preferably has a thickness in the range of 5 to 100 mil and preferably contains less than 50 wt % solvent. The wet film is preferably passed through an aeration oven where it is subjected to a drying temperature in the range of 40 to 90° C. The dry film thickness preferably should be about 50 to 90% of that of the wet film, most preferably, the dry film has a thickness between 2 and 50 mil. During the extrusion process, the temperature of the extruder should be maintained at around 40° C. and preferably should not exceed 80° C.

Solvents suitable for use in the preferred method of the present invention include aqueous solutions, alcoholic solutions and hydro-alcoholic solutions; preferably aqueous solutions, most preferably water.

The bioadhesive, closed-cell foam film, sustained release, delivery devices of the present invention may be administered to a subject by placing the film on a mucosal tissue of the subject. Upon application to a mucosal tissue, the delivery device will adhere to the mucosal tissue where it dissolves or erodes releasing an active agent or combination of active agents to the subject. This release of the active agent or combination of active agents occurs without mastication or the need for the intake of water or other liquid.

Preferably, the bioadhesive, closed-cell foam film, sustained release, delivery devices of the present invention exhibit a bioadhesive force of at least 10 grams, more preferably at least 15 grams, most preferably at least 20 grams. The delivery devices of the present invention are preferably cast to have a thickness of 2 to 50 mil.

The water content of the delivery devices of the present invention preferably ranges from 2 to 20 wt % with a more preferred range of 5 to 15 wt %.

The bioadhesive, closed-cell foam film, sustained release, delivery devices of the present invention preferably exhibit one or more of the following features: a dry film thickness in the range of 2 to 50 mils; a bioadhesive force of at least 10 grams, more preferably at least 15 grams, most preferably at least 20 grams.

EXAMPLES

The preferred embodiments of the present invention will now be further described through the following examples set forth hereinbelow which are intended to be illustrative of the preferred embodiments of the present invention and are not intended to limit the scope of the invention as set forth in the appended claims.

TABLE 1

Formulation of the Bioadhesive Delivery Devices described in Examples 1–3

| Substance | % by weight in composition | | |
|---|---|---|---|
| | Ex. 1 | Ex. 2 | Ex. 3 |
| Estradiol | 1 | 1 | 1 |
| Propylene glycol | 36 | 36 | 36 |
| Gelatin | — | 36 | — |
| Methacrylic acid-methyl methacrylate copolymer {Eudragit RL} | — | — | 36 |
| Polyvinylalcohol | 36 | — | — |
| Sodium alginate | 20 | 20 | — |
| Carrageenan | — | — | 20 |
| Sorbitan monooleate {Span 80} | 1 | — | 1 |
| Polyoxyethylene castor oil {Cremaphor EL} | — | 1 | — |
| Aspartame | 0.82 | 0.82 | 0.82 |
| Benzoic acid | 0.17 | 0.17 | 0.17 |
| Sodium EDTA | 0.17 | 0.17 | 0.17 |
| Peppermint oil | 1.70 | 1.70 | 1.70 |
| Polyoxyethylene hydrogenated castor oil {Cremaphor RH40} | 1.70 | 1.70 | 1.70 |
| Citric acid | 1.38 | 1.38 | 1.38 |
| FD&C Red #40 | qs | qs | qs |

Example 1

Bioadhesive Delivery Device Containing Estradiol

Polyvinylalcohol (nonionic polymer) and sodium alginate (anionic polymer) were dissolved in water. Hydro-ethanolic solution of sorbitan monooleate (swelling modifier) was then mixed into the polymer solution. The resulting solution was then spraydried to obtain unitorm bioadhesive microparticles. The microparticles were then well blended with estradiol (active agent), aspartame (taste modifier), benzoic acid (preservative), sodium EDTA (chelating agent), citric acid (buffering agent) and red #40 (coloring agent). Peperming oil (taste modifier) and polyoxyethylene hydrogenated castor oil (foaming agent) were dispersed into propylene glycol (softening agent). The powder blend was fed into the hopper of a twin-screw extruder. The propylene glycol mixture was then introduced into the extruder to wet the powder mixture. High-pressure air was also introduced into the extruder to generate air bubbles in the wetted mixture. The foamy mixture was forced through a ribbon die to form a wet film. The extruded film was dried and die-cut into suitable doses.

Example 2

Bioadhesive Delivery Device Containing Estradiol

Gelatin (nonionic polymer) and sodium alginate (anionic polymer) were first dissolved in water. Hydro-ethanolic solution of polyoxyethylene castor oil (swelling modifier) was then mixed into the polymer solution under agitation. The resulting solution was then spray-dried to obtain uniform bioadhesive microparticles. The microparticles were then well blended with estradiol (active agent), aspartame (taste modifier), benzoic acid (preservative), sodium EDTA (chelating agent), citric acid (buffering agent) and red #40 (coloring agent). Peppermint oil (taste modifier) and polyoxyethylene hydrogenated castor oil (foaming agent) were dispersed into propylene glycol (softening agent). The powder blend was fed into the hopper of a twin-screw extruder. The propylene glycol mixture was then introduced into the extruder to wet the powder mixture. High-pressure air was also introduced into the extruder to generate air bubbles in the wetted mixture. The foamy mixture was forced through a ribbon die to form a wet film. The extruded film was then die-cut into suitable unit doses.

Example 3

Bioadhesive Delivery Device Containing Estradiol

Methacrylic acid-methyl methacrylate copolymer (nonionic polymer) and carrageenan (anionic polymer) were first dissolved in water. Hydro-ethanolic solution of sorbitan monooleate (swelling modifier) was then mixed into the polymer solution under agitation. The resulting solution was then spray-dried to obtain uniform bioadhesive microparticles. The microparticles were then well blended with estradiol (active agent), aspartame (taste modifier), benzoic acid (preservative), sodium EDTA (chelating agent), citric acid (buffering agent) and red #40 (coloring agent). Peppermint oil (taste modifier) and polyoxyethylene hydrogenated castor oil (foaming agent) were dispersed into propylene glycol (softening agent). The powder blend was fed into the hopper of a twin-screw extruder. The propylene glycol mixture was then introduced into the extruder to wet the powder mixture. High-pressure air was also introduced into the extruder to generate air bubbles in the wetted mixture. The foamy mixture was forced through a ribbon die to form a wet film. The extruded film was dried and die-cut into suitable unit doses.

Using the standard USP Apparatus #1, unit doses obtained from each of Examples 1–3 were tested to determine the release profile for the estradiol contained therein. The results of these release profile tests are graphically displayed in FIG. 1 which depicts the percentage of estradiol released as a function of time. The results of the release profile test on unit doses obtained in Example 1 are depicted in FIG. 1 by the line connecting the circles. The results of the release profile test on unit doses from Example 2 are depicted in FIG. 1 by the line connecting the squares. The results of the release profile test on unit doses from Example 3 are depicted in FIG. 1 by the line connecting the triangles. An analysis of the results depicted in FIG. 1 will demonstrate that the bioadhesive delivery devices of Examples 1–3 exhibited a near zero order release of estradiol over their respective release periods.

The present invention having been disclosed in connection with the foregoing embodiments, additional embodiments will now be apparent to persons skilled in the art. The present invention is not intended to be limited to the embodiments specifically mentioned, and accordingly reference should be made to the appended claims rather than the foregoing discussion, to assess the spirit and scope of the present invention in which exclusive rights are claimed.

We claim:

1. A bioadhesive, closed-cell foam film, sustained release, delivery device comprising a blend comprising:
   (a) at least one active agent,
   (b) at least one nonionic polymer,
   (c) at least one anionic polymer,
   (d) at least one softening agent,
   (e) at least one swelling modifier,
   (f) at least one chelating agent,
   (g) at least one buffering agent, and
   (h) at least one foaming agent;
   wherein the blend is a closed-cell foam and wherein the delivery device is a single layer device.

2. The delivery device of claim 1, wherein the mass ratio of the at least one nonionic polymer to the at least one anionic polymer is in the range of 1:6 to 6:1.

3. The delivery device of claim 1, wherein the mass ratio of the at least one swelling modifier to a combined mass of the at least one nonionic polymer and the at least one anionic polymer is in the range of 1:100 to 1:10.

4. The delivery device of claim 1, wherein the bioadhesive, closed-cell foam has a density of at least 0.2 grams/cm$^3$.

5. A bioadhesive, closed-cell foam film, sustained release, delivery device comprising a blend comprising:
   (a) at least one active agent,
   (b) at least one nonionic polymer,
   (c) at least one anionic polymer,
   (d) at least one softening agent,
   (e) at least one swelling modifier,
   (f) at least one chelating agent,
   (g) at least one buffering agent,
   (h) at least one foaming agent; and
   (i) entrapped gas bubbles;
   wherein the blend is a closed-cell foam composition which exhibits a density that is 10 to 90% of the density of an identical non-foamed composition.

6. The delivery device of claim 1, wherein the delivery device comprises 0.01 to 50 wt % of the at least one active agent.

7. The delivery device of claim 1, wherein the delivery device comprises 10 to 60 wt % of the at least one nonionic polymer.

8. The delivery device of claim 1, wherein the delivery device comprises 10 to 60 wt % of the at least one anionic polymer.

9. The delivery device of claim 1, wherein the delivery device comprises 5 to 40 wt % of the at least one softening agent.

10. The delivery device of claim 1, wherein the delivery device comprises 0.1 to 10 wt % of the at least one swelling modifier.

11. The delivery device of claim 1, wherein the delivery device comprises 0.01 to 5 wt % of the at least one chelating agent.

12. The delivery device of claim 1, wherein the delivery device comprises 0.1 to 10 wt % of the at least one buffering agent.

13. The delivery device of claim 1, wherein the delivery device comprises 0.1 to 5 wt % of the at least one foaming agent.

14. The delivery device of claim 1, further comprising at least one additional ingredient selected from: a taste modifying agent, a coloring agent, a preservative, and a permeation enhancer.

15. A bioadhesive, closed-cell foam film, sustained release, delivery device comprising a blend comprising:
   (a) 0.01 to 50 wt % of at least one active agent,
   (b) 10 to 60 wt % of at least one nonionic polymer,
   (c) 10 to 60 wt % of at least one anionic polymer,
   (d) 5 to 40 wt % of at least one softening agent,
   (e) 0.1 to 10 wt % of at least one swelling modifier,
   (f) 0.01 to 5 wt % of at least one chelating agent,
   (g) 0.1 to 10 wt % of at least one buffering agent, and
   (h) 0.1 to 5 wt % of at least one foaming agent;
   wherein the blend is a closed-cell foam and wherein the delivery device is a single layer device.

16. The delivery device of claim 15, further comprising at least one additional ingredient selected from: a taste modifying agent, a coloring agent, a preservative, and a permeation enhancer.

17. The delivery device of claim 15, wherein the mass ratio of the at least one nonionic polymer to the at least one anionic polymer is in the range of 1:6 to 6:1.

18. The delivery device of claim 15, wherein the mass ratio of the at least one swelling modifier to a combined mass of the at least one nonionic polymer and the at least one anionic polymer is in the range of 1:100 to 1:10.

19. The delivery device of claim 15, wherein the bioadhesive, closed-cell foam has a density of at least 0.2 grams/cm$^3$.

20. The delivery device of claim 15, wherein the blend has a density in the range of 10 to 90% of the density of an identical non-foamed composition.

21. The delivery device of claim 15, wherein the delivery device is selected from the group consisting of a buccal delivery device and a vaginal delivery device.

* * * * *